(12) United States Patent
Motai

(10) Patent No.: US 11,504,127 B2
(45) Date of Patent: Nov. 22, 2022

(54) METHOD FOR ANASTOMOSING ALIMENTARY TRACT

(71) Applicant: OLYMPUS CORPORATION, Hachioji (JP)

(72) Inventor: Kosuke Motai, Hidaka (JP)

(73) Assignee: OLYMPUS CORPORATION, Tokyo (JP)

( * ) Notice: Subject to any disclaimer, the term of this patent is extended or adjusted under 35 U.S.C. 154(b) by 990 days.

(21) Appl. No.: 16/242,267

(22) Filed: Jan. 8, 2019

(65) Prior Publication Data
US 2020/0214709 A1    Jul. 9, 2020

(51) Int. Cl.
| | | |
|---|---|---|
| *A61B 17/11* | (2006.01) | |
| *A61B 17/115* | (2006.01) | |
| *A61B 34/20* | (2016.01) | |
| *A61B 1/313* | (2006.01) | |
| *A61B 17/29* | (2006.01) | |
| *A61B 1/273* | (2006.01) | |
| *A61B 1/005* | (2006.01) | |
| *A61B 1/00* | (2006.01) | |

(52) U.S. Cl.
CPC ......... *A61B 17/1114* (2013.01); *A61B 1/005* (2013.01); *A61B 1/0014* (2013.01); *A61B 1/273* (2013.01); *A61B 1/3132* (2013.01); *A61B 17/1155* (2013.01); *A61B 17/29* (2013.01); *A61B 34/20* (2016.02); *A61B 17/115* (2013.01); *A61B 2017/1125* (2013.01); *A61B 2017/1139* (2013.01); *A61B 2034/2055* (2016.02)

(58) Field of Classification Search
CPC ............. A61B 17/1114; A61B 17/1155; A61B 1/0014; A61B 1/005; A61B 1/273; A61B 2017/1139; A61B 2017/00296; A61B 1/00119; A61B 1/00121; A61B 1/00128; A61B 1/00087
See application file for complete search history.

(56) References Cited

U.S. PATENT DOCUMENTS

| | | | |
|---|---|---|---|
| 8,777,840 B2 * | 7/2014 | Belafsky | A61B 1/0014 600/128 |
| 2014/0151429 A1 * | 6/2014 | Scheib | A61B 17/068 227/175.1 |
| 2017/0000475 A1 * | 1/2017 | Sgroi, Jr. | A61B 17/0469 |

FOREIGN PATENT DOCUMENTS

JP    2003-019138 A    1/2003

* cited by examiner

*Primary Examiner* — Katherine H Schwiker
*Assistant Examiner* — Serenity A Miller
(74) *Attorney, Agent, or Firm* — Oliff PLC

(57) ABSTRACT

A method for anastomosing an alimentary tract according to a first aspect of the invention includes a first step of inserting an endoscope into an alimentary tract through a natural opening in a state where a distal end part of a tube body is coupled to an outer periphery of a distal end part of the endoscope; a second step of making a hole in a tract wall of the alimentary tract; a third step of inserting the tube body through the hole; a fourth step of grasping the distal end part of the tube body disposed through the hole; a fifth step of separating the tube body from an outer periphery of the distal end part of the endoscope; and a sixth step of delivering the treatment part up to the hole after the fifth step.

4 Claims, 12 Drawing Sheets

METHOD FOR ANASTOMOSING ALIMENTARY TRACT

TECHNICAL FIELD OF THE INVENTION

The present invention relates to a method for anastomosing an alimentary tract.

RELATED ART

In recent years, staple instruments (staplers) are used in surgery in which hollow organs, such as alimentary tracts, are anastomosed. By using a suitable staple instrument, the surgery in which hollow organs, such as alimentary tracts, are anastomosed can be facilitated, and surgery time can be markedly shortened.

Japanese Unexamined Patent Application, First Publication No. 2003-019138 discloses a tissue suture ligator in which tubular suturing is easy. In the tissue suture ligator, an insertion part has flexibility, insertion is easy even in bent organs, such as the large intestine, and physical burden on patients is low.

SUMMARY OF THE INVENTION

A method for anastomosing an alimentary tract according to a first aspect of the invention is a method for anastomosing an alimentary tract, using an endoscope, and a tube body having a distal end part and a proximal end part, the distal end part being coupled to an outer periphery of a distal end part of the endoscope, and the proximal end part being provided with a treatment part that treats a tract wall of an alimentary tract. The method includes a first step of inserting the endoscope into the alimentary tract through a natural opening in a state where the distal end part of the tube body is coupled to the outer periphery of the distal end part of the endoscope; a second step of making a hole to allow an abdominal cavity and an inside of the alimentary tract to communicate with each other in the tract wall of the alimentary tract; a third step of moving the distal end part of the endoscope to insert the tube body through the hole; a fourth step of grasping the distal end part of the tube body disposed through the hole by grasping forceps percutaneously introduced into the abdominal cavity; a fifth step of separating the tube body from an outer periphery of the distal end part of the endoscope by moving the distal end part of the endoscope in a direction away from the grasping forceps in a state where the distal end part of the tube body is grasped by the grasping forceps; and a sixth step of delivering the treatment part up to the hole by pulling the tube body with the grasping forceps after the fifth step.

EMBODIMENTS OF THE INVENTION

First Embodiment

Figure 1:
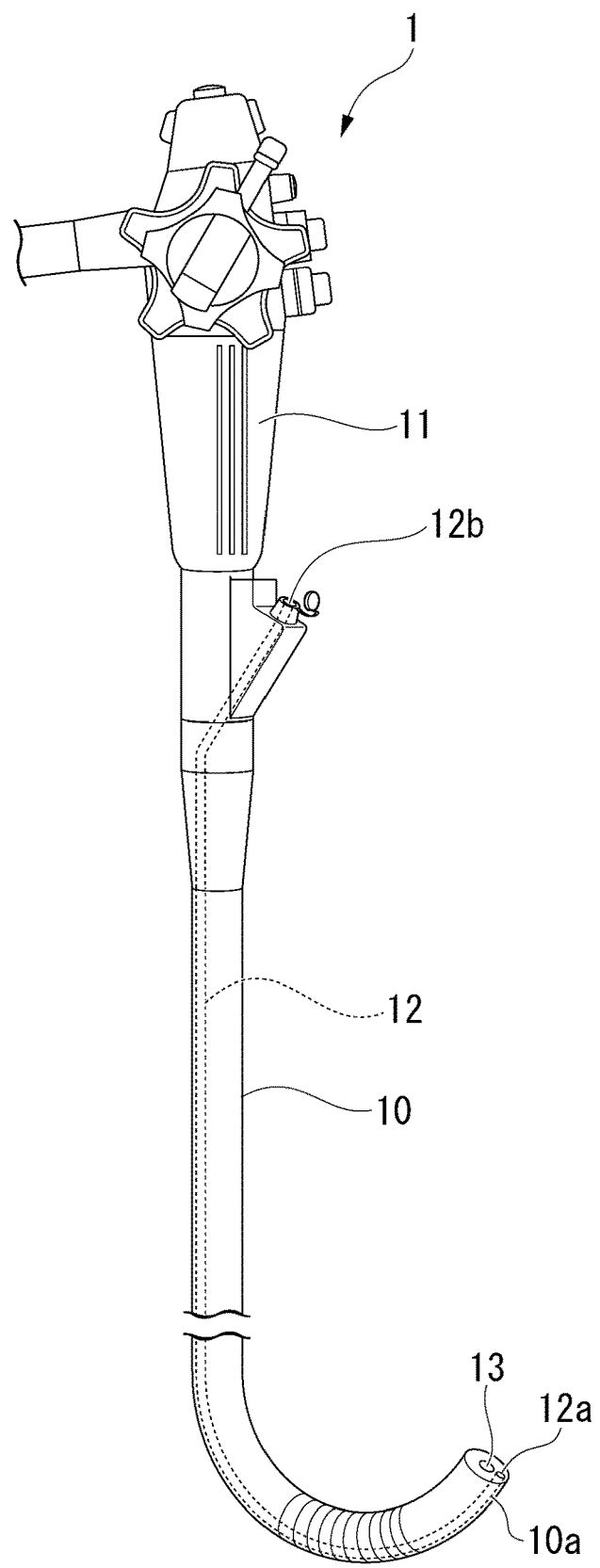
FIG. 1 is a view illustrating an overall configuration of an endoscope to be used in a method for anastomosing an alimentary tract according to a first embodiment of the invention.
Figure 2:
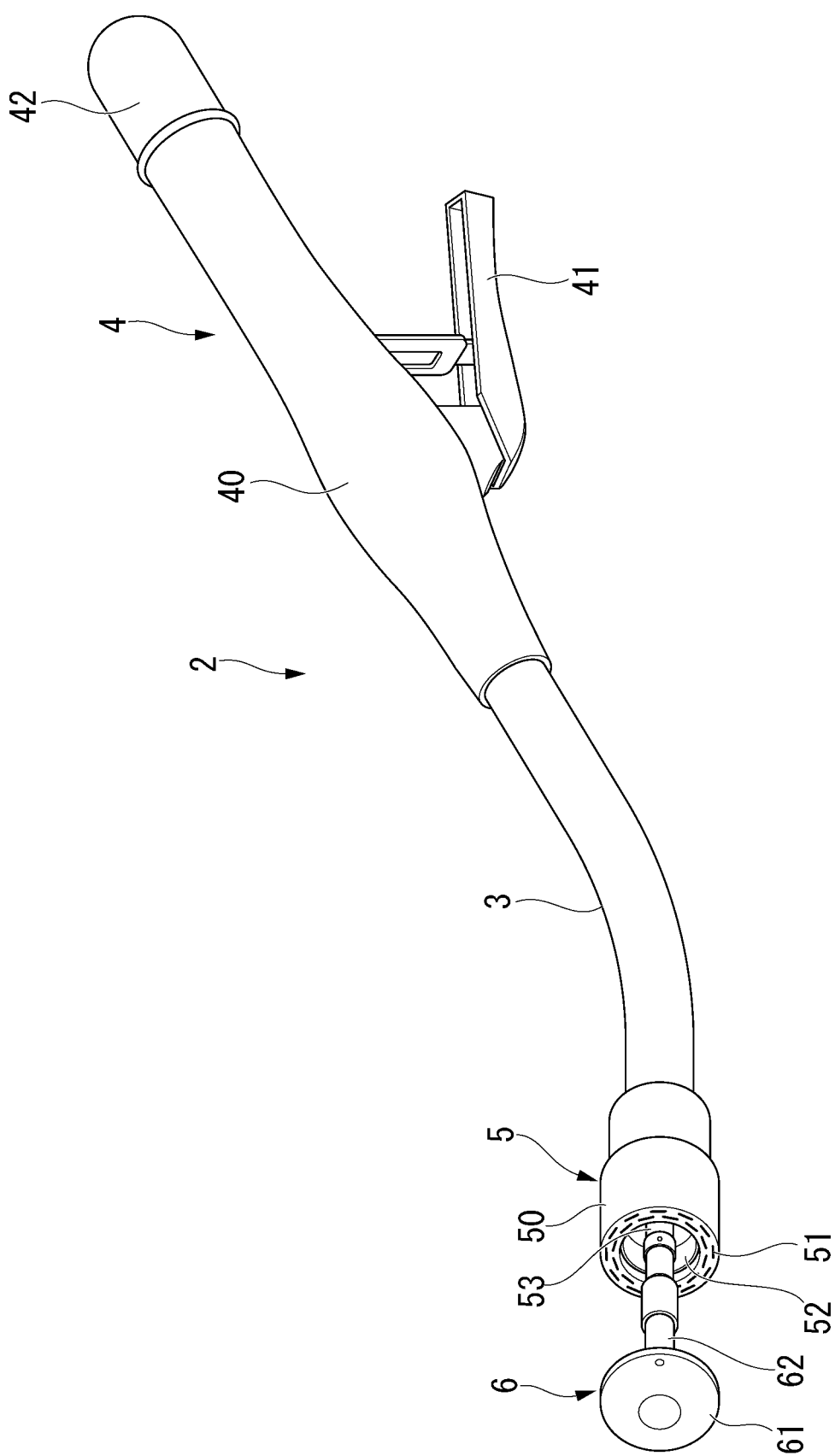
FIG. 2 is a view illustrating an overall configuration of a stapler to be used in the method of anastomosing an alimentary tract.

A method for anastomosing an alimentary tract according to a first embodiment of the invention will be described with reference to FIGS. 1 to 13. FIG. 1 is a view illustrating an overall configuration of an endoscope 1 to be used in the method for anastomosing an alimentary tract according to the present embodiment. FIG. 2 is a view illustrating an overall configuration of a stapler 2 to be used in the method for anastomosing an alimentary tract according to the present embodiment.

[Endoscope 1]

A surgeon can select and use any one from a well-known endoscope to be orally inserted into the alimentary tract. As illustrated in FIG. 1, the endoscope 1 to be used in the present embodiment includes an insertion part 10 to be inserted into a body cavity, a body operating part 11 provided at a proximal end of the insertion part 10, and an imaging unit 13 provided at a distal end of the insertion part 10.

A distal end opening 12a of a treatment tool insertion channel 12 opens at a distal end part 10a of the insertion part 10. The treatment tool insertion channel 12 is a passage that extends over the entire length of the insertion part 10 from the distal end opening 12a, and a proximal end part thereof is connected to a treatment tool introduction part 12b provided in the body operating part 11. A treatment tool having a treatment part, such as a high-frequency knife or grasping forceps, at a distal end thereof is inserted into the treatment tool insertion channel 12.

The imaging unit 13 has an imaging element that images internal organs of a treatment target. Imaging data captured by the imaging unit 13 is transmitted to an external image processor via the body operating part 11. The imaging data transmitted to the image processor is subjected to image processing and is displayed on a monitor.

[Stapler 2]

The surgeon can select and use any one from a well-known circular stapler that annularly sutures a hollow organ, such as the alimentary tract. As illustrated in FIG. 2, the stapler 2 to be used in the present embodiment includes a stapler body 3, and an anvil kit 6.

The stapler body 3 has a handle 4 provided at a proximal end of the stapler body 3, and a staple discharge part 5 attached at a distal end of the stapler body 3.

As illustrated in FIG. 2, the handle 4 has a handle body 40, a firing handle 41, and an adjusting knob 42.

As illustrated in FIG. 2, the staple discharge part 5 has a cylindrical housing 50, a staple holder 51 that is provided in an annular shape on a front end face of the housing 50, a cutter 52 that is provided in an annular shape on the front end face of the housing 50, and an anvil shaft 53 that extends along a central axis in a longitudinal axis direction of the housing 50.

The staple holder 51 is capable of storing staple needles and is disposed in two rows in an annular shape on the front end face of the housing 50. The staple needles are bent in a U-shape and are stored in the staple holder 51 in a state where sharp parts at distal ends thereof face the front end face of the housing 50. The staple needles stored in the staple holder 51 are discharged from the front end face of the housing 50 by operating the firing handle 41.

The cutter 52 is provided in an annular shape nearer to the inner peripheral side than the staple holder 51 on the front end face of the housing 50. By operating the firing handle 41, the cutter 52 is protruded from the front end face of the housing 50.

The anvil shaft 53 is a member that holds the anvil kit 6. By operating the adjusting knob 42, the anvil shaft 53 is moved forward and backward in the longitudinal axis direction.

Figure 3:
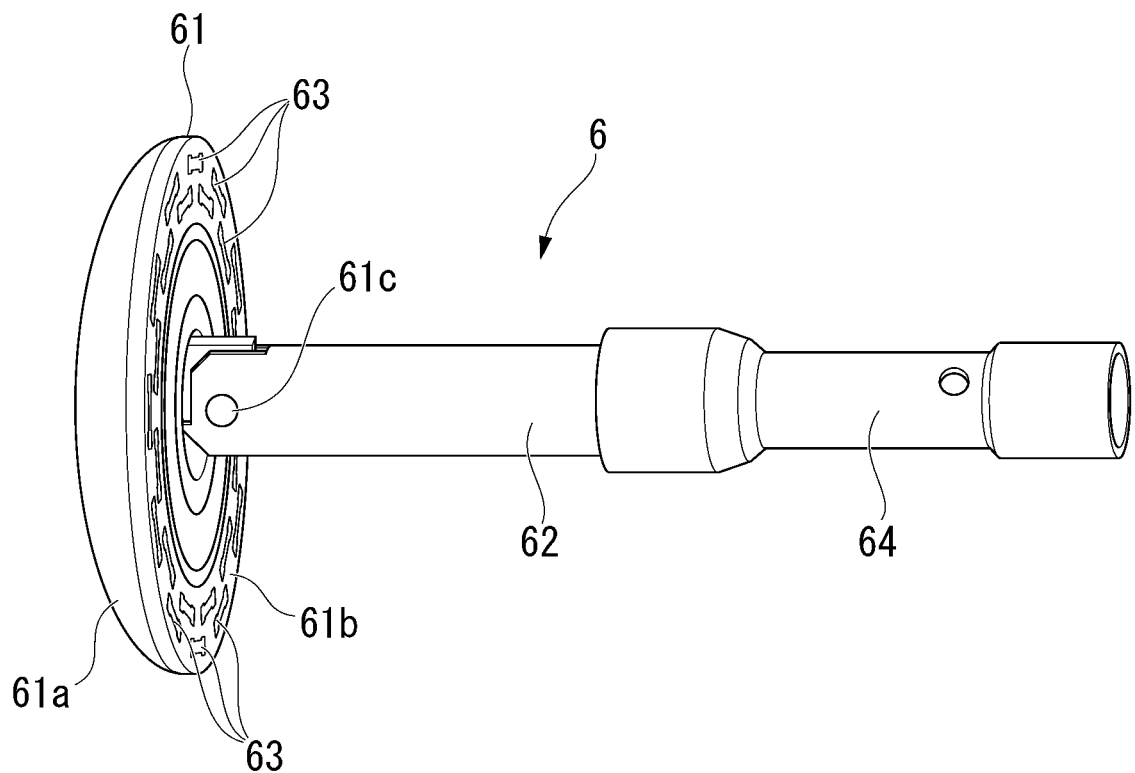
FIG. 3 is a view illustrating an overall configuration of an anvil kit of the stapler.
Figure 4:
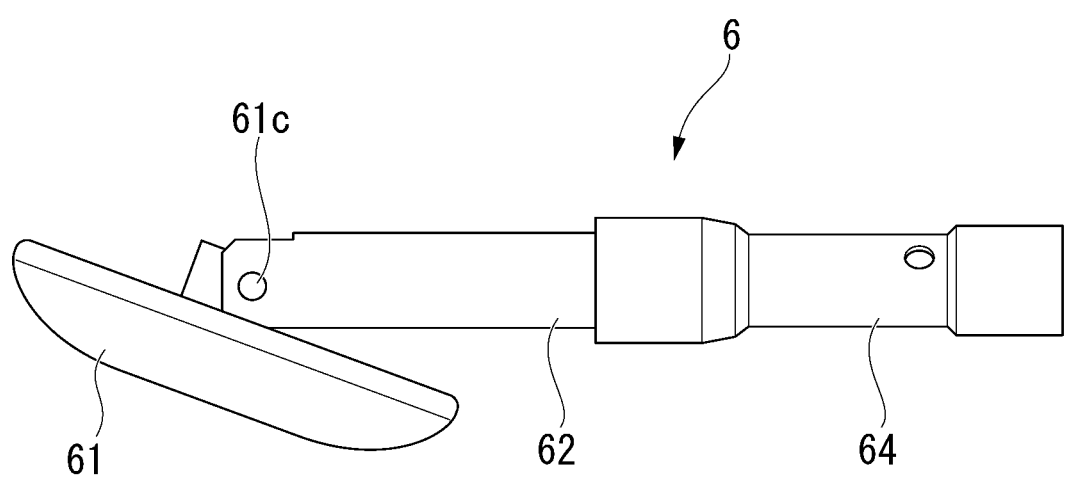
FIG. 4 is a view illustrating an overall configuration of the anvil kit of the stapler.

FIGS. 3 and 4 are views illustrating an overall configuration of the anvil kit 6. The anvil kit (treatment part) 6 has an anvil head 61 capable of receiving staple needles to be discharged from the staple discharge part 5, and the anvil shaft 62.

The anvil head 61 is a disk-shaped member, and has a convex surface 61a formed in a dome shape on a distal end side thereof, and a tissue contact surface 61b on a proximal end side thereof. The tissue contact surface 61b is provided with a plurality of pockets 63 capable of receiving the staple needles discharged from the staple holder 51. As illustrated in FIG. 3, the plurality of pockets 63 are disposed in two rows in an annular shape along the tissue contact surface 61b of the anvil head 61.

An attachment member 61c is provided at the center of the tissue contact surface 61b of the anvil head 61. The attachment member 61c is pivotably engaged with the anvil shaft 62, and the anvil head 61 is pivotably attached to the anvil shaft 62. The anvil head 61 illustrated in FIG. 4 is disposed at a position where the anvil head 61 is tilted with respect to the anvil shaft 62.

The anvil shaft 62 is a shaft member attachable to and detachable from the anvil shaft 53. The anvil shaft 62 has the anvil head 61 attached to a distal end thereof and has a fitting part 64 attachable to and detachable from the anvil shaft 53 at a proximal end thereof.

By operating the adjusting knob 42 by the surgeon, the anvil kit 6 can be moved forward and backward with respect to the staple discharge part 5. By bringing the anvil kit 6 close to the staple discharge part 5, tissues to be anastomosed can be sandwiched by the staple discharge part 5 and the tissue contact surface 61b of the anvil kit 6.

By operating the firing handle 41 by the surgeon, the plurality of staple needles can be discharged from the staple discharge part 5. The staple needles are driven into the tissues sandwiched between the staple discharge part 5 and the anvil kit 6. Additionally, simultaneously when the staple needles are discharged, the cutter 52 moves forward and cuts the tissues sandwiched between the staple discharge part 5 and the tissue contact surface 61b of the anvil kit 6 in an annular shape.

[Delivery System 100]

Figure 5:
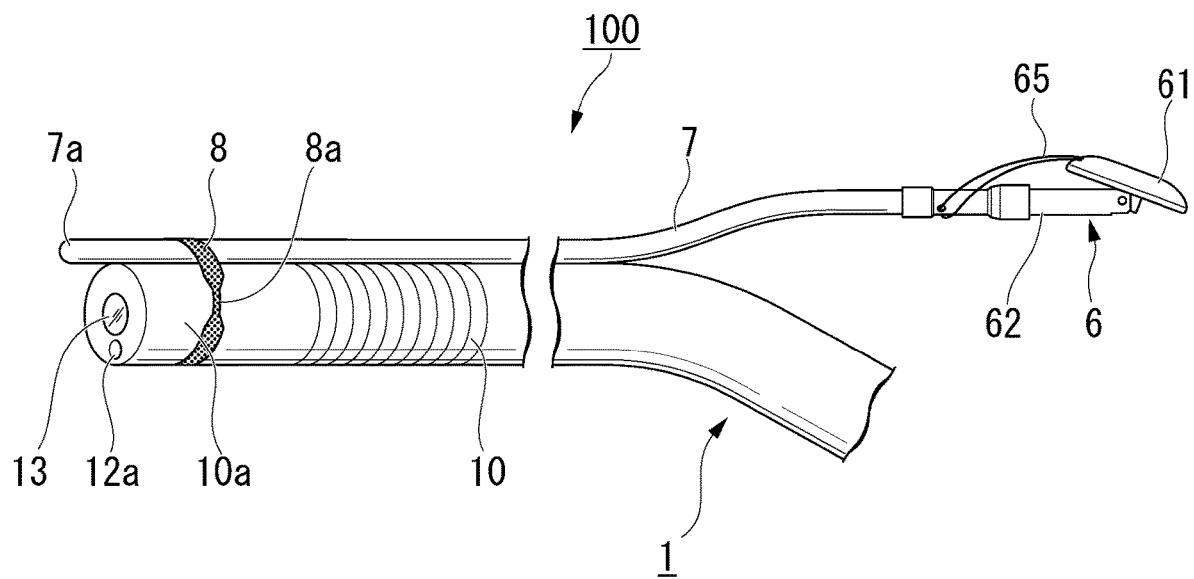
FIG. 5 is a view illustrating a configuration of a delivery system to be used in the method of anastomosing an alimentary tract.

FIG. 5 is a view illustrating a configuration of a delivery system 100 to be used in the method for anastomosing an alimentary tract according to the present embodiment. The delivery system 100 includes the endoscope 1, the anvil kit 6, a tube body 7, and a binding band 8. The anvil kit 6 of the delivery system 100 is the anvil kit 6 detached from the stapler 2.

The tube body 7 is a hollow elongated member formed of a material having elasticity, and has the anvil shaft 62 of the anvil kit 6 detachably attached to a distal end thereof. The anvil head 61 is fixed to a position where the anvil head 61 is tilted with respect to the anvil shaft 62 by a string 65.

The binding band 8 couples a distal end part 7a of the tube body 7 to an outer periphery of the distal end part 10a of the insertion part 10. A portion of the binding band 8 is provided with an easily breakable part 8a capable of being intentionally broken. The easily breakable part 8a has a smaller cross-sectional area and is more easily broken, as compared to other portions of the binding band 8.

The binding band 8 is colored in a color (for example, black) that is easily observed in a living body, and the surgeon can easily distinguish between a living body portion and the binding band 8 and recognize the living body portion and the binding band 8 in a case where the binding band 8 is imaged by the imaging unit 13 of the endoscope 1.

The easily breakable part 8a of the binding band 8 is formed only in one location of the binding band 8. For that reason, the binding band 8 in which the easily breakable part 8a is broken is not separated into two and is easily collected.

The coupling between the endoscope 1 and the tube body 7 by the binding band 8 is only at the distal ends. For that reason, angle operation of the endoscope 1 is not disturbed by the tube body 7. Additionally, the distal end part 7a of the tube body 7 protrudes further toward the distal end side than the distal end part 10a of the insertion part 10. For that reason, the surgeon can image the distal end part 7a of the tube body 7 with the imaging unit 13 to check the obtained image with a monitor.

[Method for Anastomosing Alimentary Tract]

Next, the details of the method for anastomosing an alimentary tract according to the present embodiment will be described. A procedure in which a colon C and an ileum (separate alimentary tract) I, which are separated due to excision of lesions by a linear stapler, are anastomosed together will be described as an example. In addition, the method for anastomosing an alimentary tract according to the present embodiment is not limited to the example shown below, and can be used for the alimentary tract into which the endoscope is transluminally inserted.

The surgeon inserts a laparoscope L, abdominal cavity forceps F, a linear stapler (not shown), and the like into an abdominal cavity A from separate holes made in the abdominal wall, and excises the lesion locations of the colon C and the ileum I with the linear stapler. Since the lesion locations are excised from both sides of the stomach side and the anus side, an end part E1 of the colon C and an end part E2 of the ileum I that are sutured together by the linear stapler are separated.

[First Step]

In a first step, the surgeon inserts the insertion part 10 of the endoscope 1 into the colon C through a natural opening from the anus in a state where the distal end part 7a of the tube body 7 of the delivery system 100 is coupled to the outer periphery of the distal end part 10a of the endoscope 1. The surgeon brings the distal end part 10a of the insertion part 10 close to a predetermined anastomosis position while bending the insertion part 10 if necessary.

[Second Step]

Figure 6:
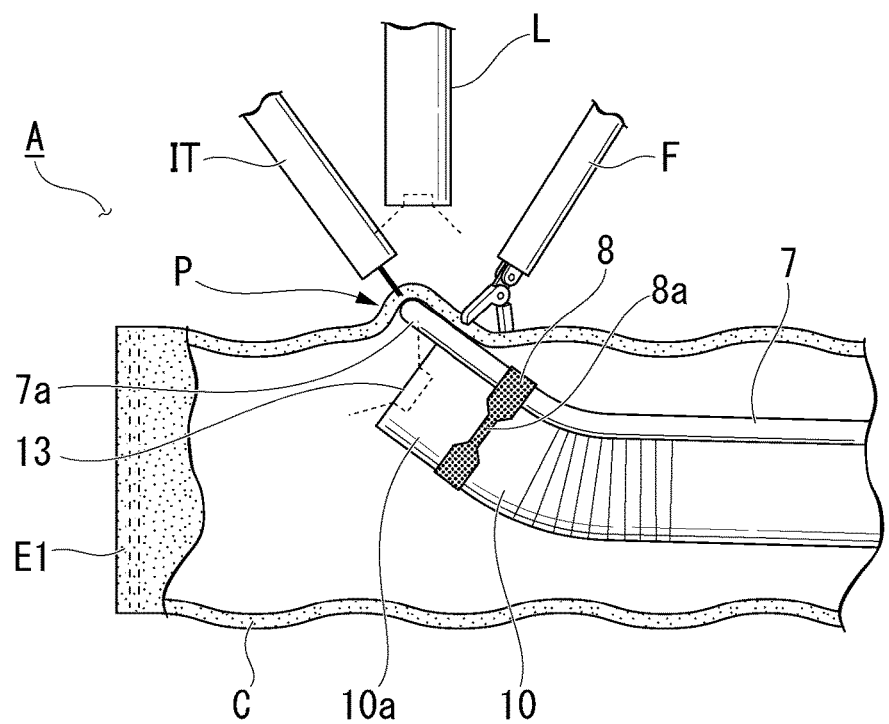
FIG. 6 is a view illustrating a second step of the method of anastomosing an alimentary tract.

FIG. 6 is a view illustrating a second step of the method of anastomosing an alimentary tract.

In the second step, the surgeon makes a hole H1 to allow the abdominal cavity A and the inside of the colon C to communicate with each other, at a predetermined anastomosis position of the a tract wall of the colon C. The hole H1 formed at the predetermined anastomosis position is formed in a location different from the end part E1 of the colon C sutured by linear stapler.

The surgeon ascertains the predetermined anastomosis position on a screen image of the inside of the colon C captured by the endoscope 1, for example, by tapping the predetermined anastomosis position of the colon C with the abdominal cavity forceps F from the abdominal cavity A side. On the basis of the screen image captured by the endoscope 1, the surgeon operates (angle operation or twisting operation) the endoscope 1 to align the position of the distal end part 10a of the endoscope 1 with the predetermined anastomosis position.

In addition, in a case where the alignment performed by moving the endoscope 1 is difficult, the intestinal tract may be moved using the abdominal cavity forceps F, and the predetermined anastomosis position may be aligned with the distal end part 10a of the endoscope 1.

As illustrated in FIG. 6, the surgeon lifts up an outer wall of the colon C by pressing the distal end part 7a of the tube body 7 against an inner wall of the colon C, ascertains a position P where the outer wall of the colon C is lifted up, and forms the hole H1 at the lifted position P on the outer wall with an incision tool IT, such as a high-frequency knife percutaneously introduced into the abdominal cavity A. The diameter dimension of the hole H1 is a dimension such that the tube body 7 and the anvil shaft 62 can be passed through the hole H1. Additionally, in order to prevent widening in a radial direction, it is desirable that the hole H1 not be a hole formed by being deeply cut in a slit shape but a hole formed in a circular shape.

When the surgeon makes the hole H1, as illustrated in FIG. 6, occurrence of deviation of a position where the hole H1 is formed can be suitably prevented by fixing the position of the colon C using the abdominal cavity forceps F.

[Third Step]

In a third step, the surgeon moves the distal end part 10a of the endoscope 1, and inserts the distal end part 7a of the tube body 7 through the hole H1. The distal end part 7a of the tube body 7 is protruded toward the abdominal cavity A side from the hole H1.

[Fourth Step]

Figure 7:
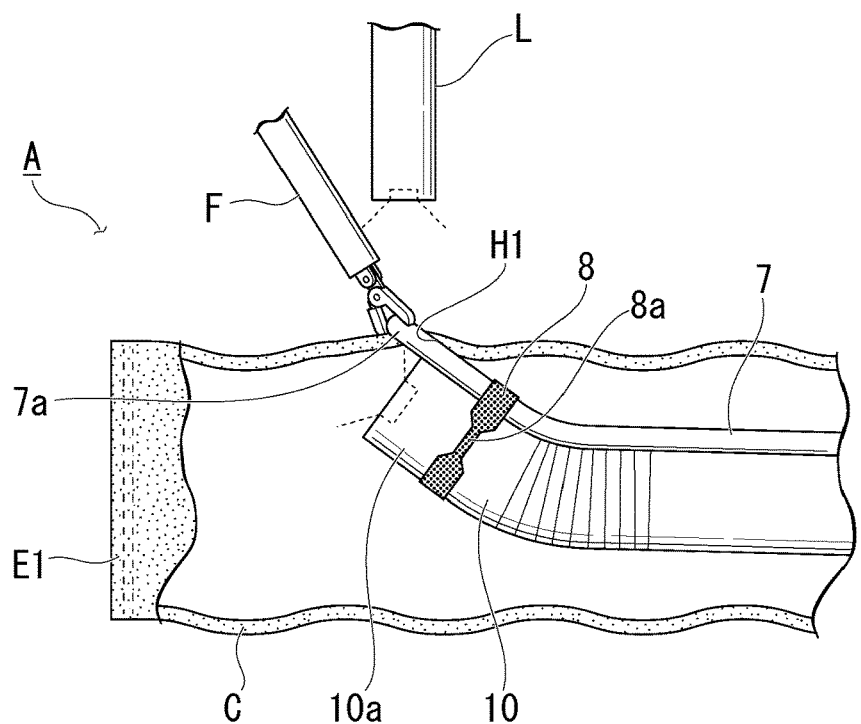
FIG. 7 is a view illustrating a fourth step of the method of anastomosing an alimentary tract.

FIG. 7 is a view illustrating a fourth step of the method of anastomosing an alimentary tract.

In the fourth step, the surgeon grasps the distal end part 7a of the tube body 7 disposed through the hole H1 by the abdominal cavity forceps F percutaneously introduced into the abdominal cavity A. Since the tube body 7 is hollow, the surgeon can easily grasp the distal end part 7a of the tube body 7.

[Fifth Step]

Figure 8:
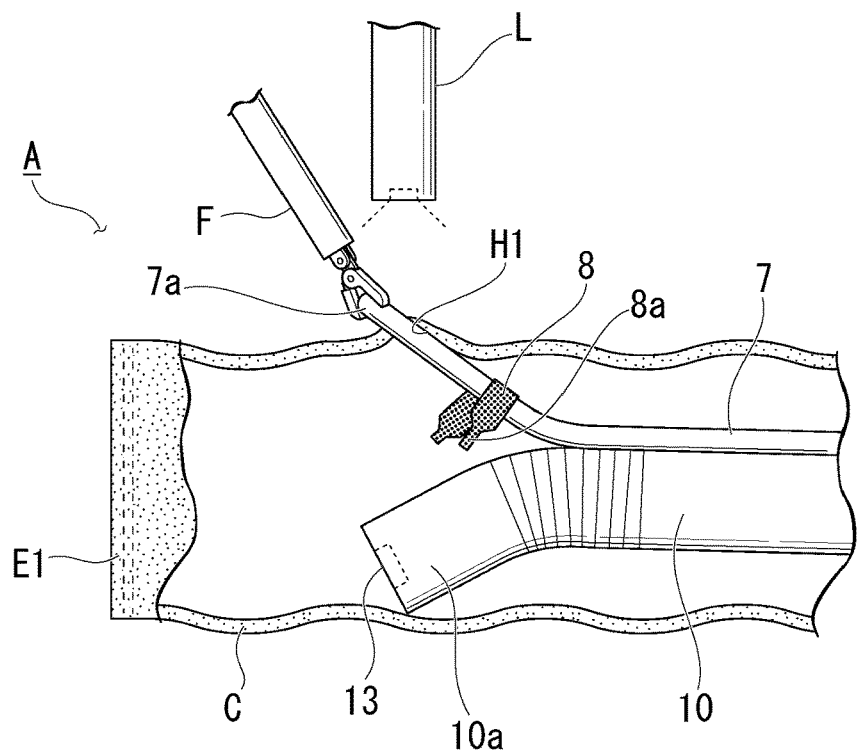
FIG. 8 is a view illustrating a fifth step of the method of anastomosing an alimentary tract.

FIG. 8 is a view illustrating a fifth step of the method of anastomosing an alimentary tract.

In the fifth step, the surgeon separates the tube body 7 from the outer periphery of the distal end part 10a of the endoscope 1 by moving the distal end part 10a of the endoscope 1 in a direction away from the abdominal cavity forceps F in a state where the distal end part 7a of the tube body 7 is grasped by the abdominal cavity forceps F. The surgeon spaces the distal end part 7a of the tube body 7 and the distal end part 10a of the endoscope 1 apart from each other by pulling the distal end part 7a of the tube body 7 grasped by the abdominal cavity forceps F toward the abdominal cavity A side. Additionally, the surgeon may space the distal end part 7a of the tube body 7 and the distal end part 10a of the endoscope 1 apart from each other by moving the distal end part 10a of the endoscope 1 in a direction away from the hole H1.

When the surgeon pulls the distal end part 7a of the tube body 7 grasped by the abdominal cavity forceps F toward the abdominal cavity A side, the distal end part 7a of the tube body 7 can be easily pulled out toward the abdominal cavity A side by fixing the position of the colon C using separate abdominal cavity forceps F.

The distal end part 7a of the tube body 7 and the distal end part 10a of the endoscope 1 are spaced apart from each other, and the easily breakable part 8a of the binding band 8 is broken. Since the binding band 8 is colored in a color (for example, black) that is easily observed in a living body, the surgeon can easily check that the easily breakable part 8a of the binding band 8 is broken from an image captured by the imaging unit 13 of the endoscope 1.

The binding band 8 is attached to the tube body 7, and the binding band 8 in which the easily breakable part 8a is broken is collected from the abdominal cavity A side together with the tube body 7 later.

In addition, the binding band 8 may not be attached to the tube body 7 or the endoscope 1. In that case, the binding band 8 in which the easily breakable part 8a is broken is collected by grasping forceps inserted into the treatment tool insertion channel 12 of the endoscope 1.

[Sixth Step]

Figure 9:
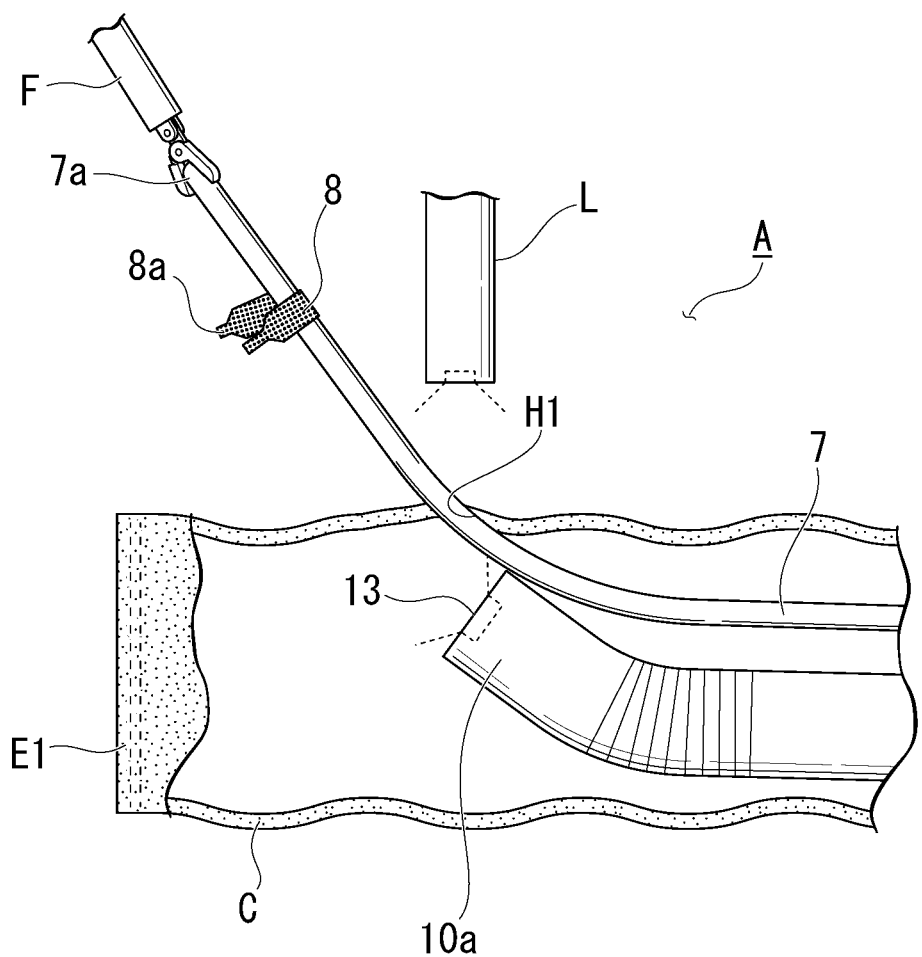
FIG. 9 is a view illustrating a sixth step of the method of anastomosing an alimentary tract.
Figure 10:
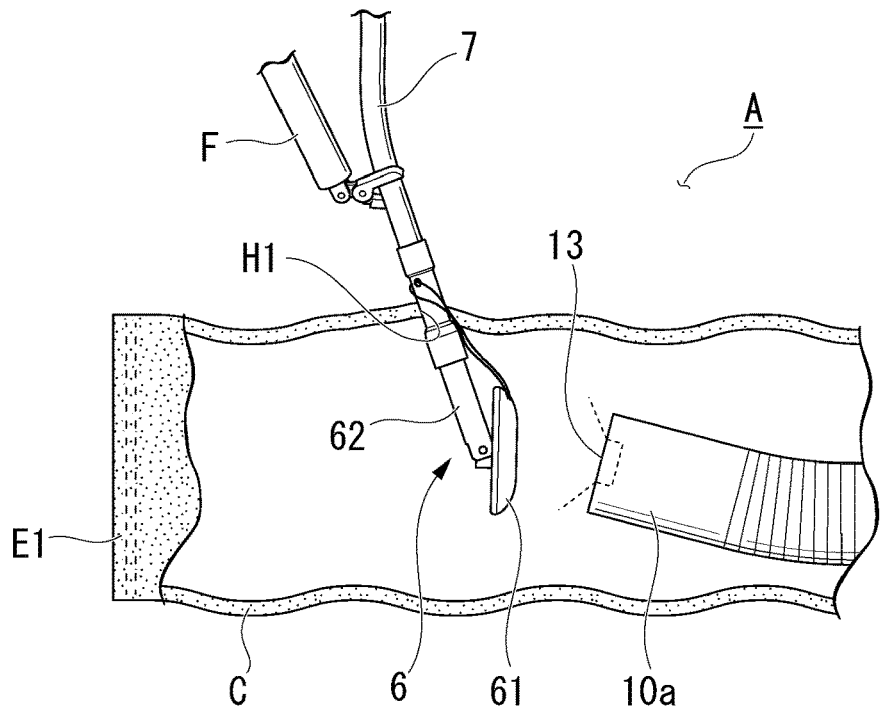
FIG. 10 is a view illustrating the sixth step of the method of anastomosing an alimentary tract.

FIGS. 9 and 10 are views illustrating a sixth step of the method for anastomosing an alimentary tract.

In the sixth step to be carried out after the fifth step, as illustrated in FIG. 9, the surgeon delivers the anvil kit (treatment part) 6 up to the hole H1 by pulling the distal end part 7a of the tube body 7 with the abdominal cavity forceps F. As illustrated in FIG. 10, the surgeon inserts the anvil shaft 62 through the hole H1 by further pulling the distal end part 7a of the tube body 7 with the abdominal cavity forceps F.

[Seventh Step]

Figure 11:
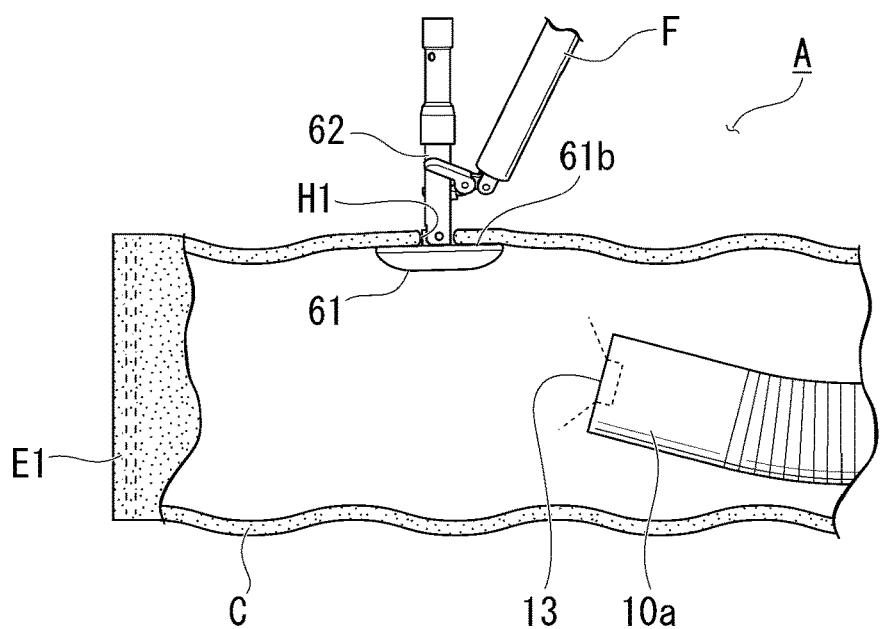
FIG. 11 is a view illustrating a seventh step of the method of anastomosing an alimentary tract.

FIG. 11 is a view illustrating a seventh step of the method for anastomosing an alimentary tract.

The surgeon detaches the string 65 attached to the anvil head 61 from the abdominal cavity A side. The anvil head 61 is pivotable with respect to the anvil shaft 62. As illustrated in FIG. 11, the surgeon pulls the tube body 7 by the abdominal cavity forceps F that has grasped the tube body 7 until the anvil head 61 abuts against the inner wall of the colon C around the hole H1. Here, since the diameter dimension of the hole H1 is such a dimension that the anvil shaft 62 can be inserted through the hole H1 but the anvil head 61 cannot be inserted therethrough, the tissue contact surface 61*b* of the anvil head 61 abuts against the inner wall of the colon C. Since the diameter dimension of the hole H1 is about the diameter dimension of the anvil shaft 62, it is not necessary to perform purse string suture in the tissue around the hole H1.

[Eighth Step]

Figure 12:
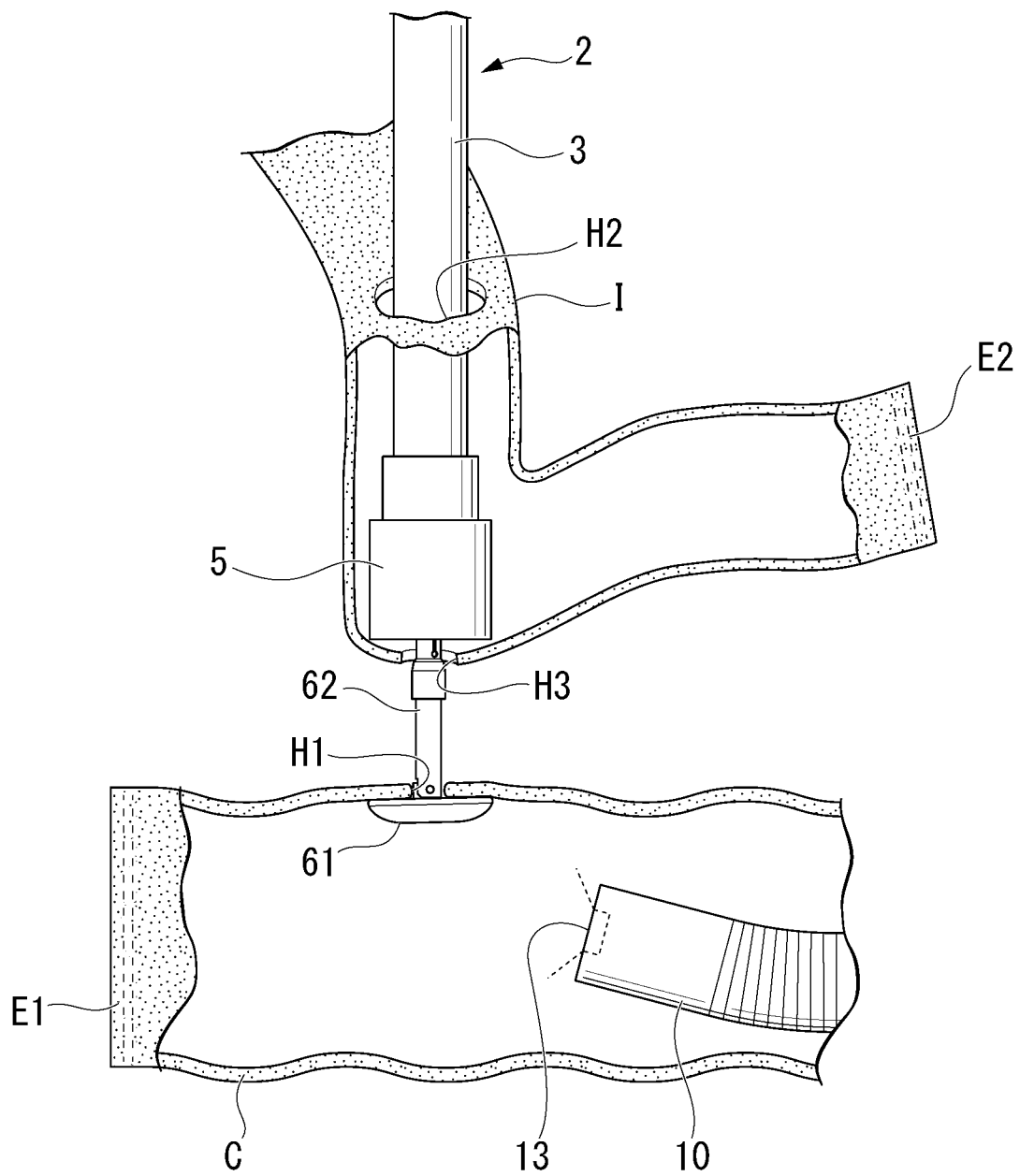
FIG. 12 is a view illustrating an eighth step of the method of anastomosing an alimentary tract.

FIG. 12 is a view illustrating an eighth step of the method of anastomosing an alimentary tract.

The surgeon inserts the stapler 2 that does not include the anvil kit 6 into the abdominal cavity A, and inserts the stapler body 3 of the stapler 2 into the ileum I from a hole H2 formed in the ileum (separate alimentary tract) I.

The surgeon inserts the anvil shaft 62 through a hole H3 formed at a predetermined anastomosis position on the ileum i side after the tube body 7 and the anvil shaft 62 are separated from each other. Since the diameter dimension of the hole H3 is about the diameter dimension of the anvil shaft 62, it is not necessary to perform purse string suture in the tissue around the hole H3.

As illustrated in FIG. 12, the surgeon couples the anvil shaft 62 to the anvil shaft 53 of the stapler 2 within the ileum I. As the surgeon operates the adjusting knob 42, the anvil kit 6 is brought close to the staple discharge part 5, and tissues of the colon C and the ileum I to be anastomosed are sandwiched by the staple discharge part 5 and the tissue contact surface 61*b* of the anvil kit 6.

The surgeon anastomoses the colon C and the ileum I by discharging staple needles to the pockets of the anvil head from the staple discharge part 5 in a state where the anvil shaft 62 and the stapler 2 are coupled (docked) together within the ileum I. Additionally, simultaneously when the staple needles are discharged, the cutter 52 moves forward and cuts the tissues sandwiched between the staple discharge part 5 and the tissue contact surface 61*b* of the anvil kit 6 in an annular shape.

Figure 13:
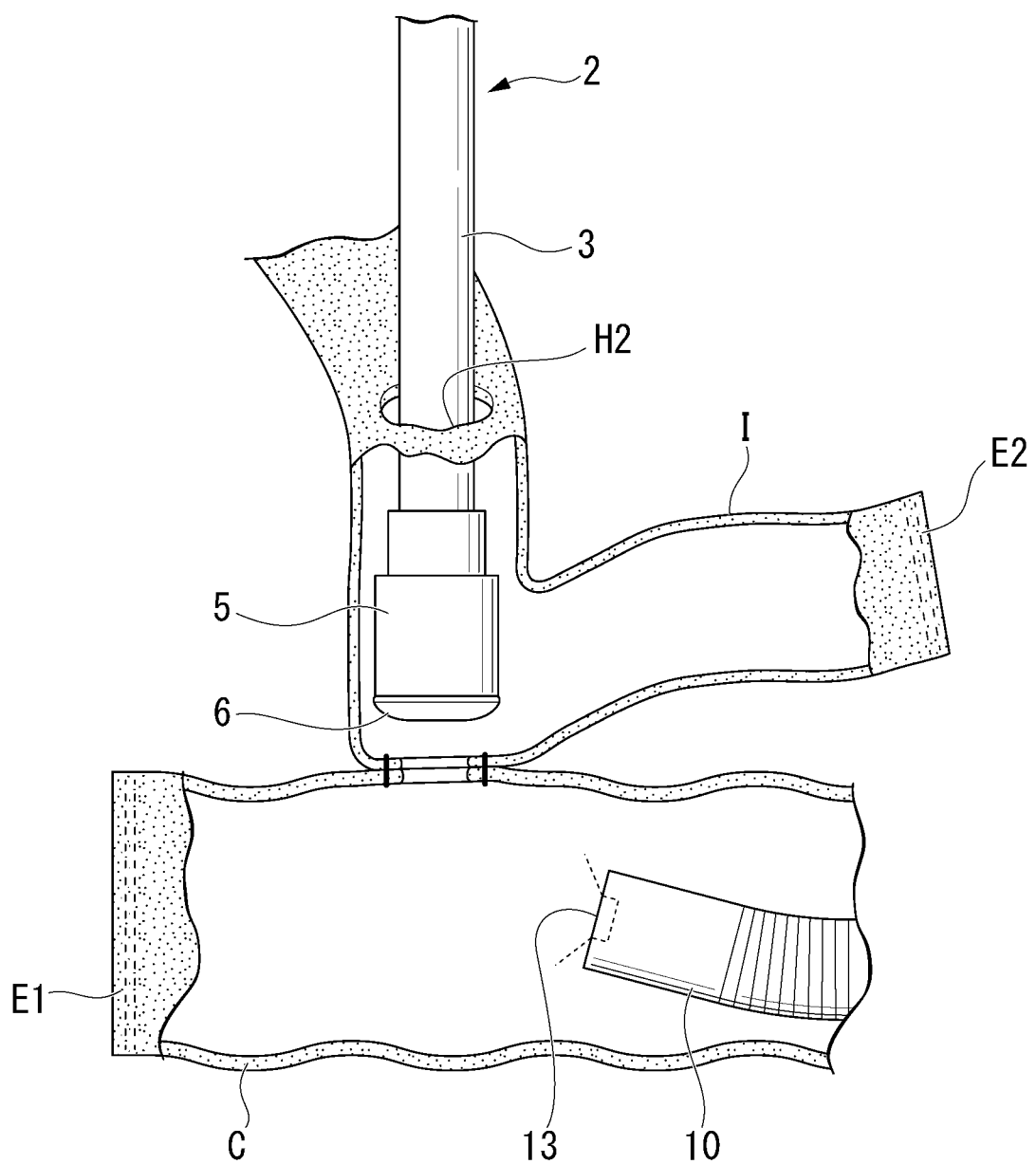
FIG. 13 is a view illustrating the colon and the ileum after the eighth step of the method of anastomosing an alimentary tract.

FIG. 13 is a view illustrating the colon C and the ileum I after the eighth step of the method for anastomosing an alimentary tract.

The surgeon can check an anastomosis part rapidly using the endoscope 1 located within the colon C. The surgeon pulls out the stapler body 3 from the ileum I, and sutures the hole H2 formed in the ileum I.

According to the method for anastomosing an alimentary tract of the present embodiment, the anvil kit (treatment part) 6 can be easily delivered to the predetermined anastomosis position. Even in a case where the alimentary tract into which the delivery system 100 is inserted through a natural opening has a complicated shape, the surgeon can insert the delivery system 100 while checking an image captured by the endoscope 1, and can deliver the anvil kit (treatment part) 6 easily to the predetermined anastomosis position.

According to the method for anastomosing an alimentary tract of the present embodiment, the anvil kit (treatment part) 6 is inserted from the colon C side, and the stapler body 3 is inserted from the ileum (separate alimentary tract) I side. For that reason, the diameter dimensions of the hole H1 and the hole H3 through which the anvil shaft 62 is inserted during anastomosis may be minimum sizes such that the anvil shaft 62 is insertable through the holes. Since the diameter dimensions of the hole H1 and the hole H3 are small, the purse string suture of tissues around the holes becomes unnecessary during anastomosis.

According to the method for anastomosing an alimentary tract of the present embodiment, locations different from the end part E1 of the colon C and the end part E2 of the ileum I, which have been sutured by the linear stapler, are anastomosed by the stapler 2. For that reason, a "double staple line" in which a track (staple line) of staple needles driven in by the linear stapler and a track (staple line) of staple needles driven in by the stapler 2 intersect each other is not formed. For that reason, an anastomosis failure resulting from the formation of the double staple line does not occur.

According to the method for anastomosing an alimentary tract of the present embodiment, an anastomosis state after anastomosis treatment can be immediately checked after the anastomosis treatment by the endoscope 1 in addition to the laparoscope L.

Although the first embodiment of the invention has been described above in detail with reference to the drawings, a specific configuration is not limited to these embodiments, and design changes are also included without departing from the scope of the invention. Additionally, the constituent elements illustrated in the above-described embodiment and modification examples can be suitably configured in combination.

Modification Example 1

For example, although the method for anastomosing an alimentary tract according to the above embodiment is used for the anastomosis of separated alimentary tracts after the excision of a lesion, the aspect of the method for anastomosing an alimentary tract according to the invention is not limited to this. The method for anastomosing an alimentary tract according to the invention can also be used for, for example anastomosis for anatomical change, such as bypass surgery of an alimentary tract.

Modification Example 2

Figure 14:
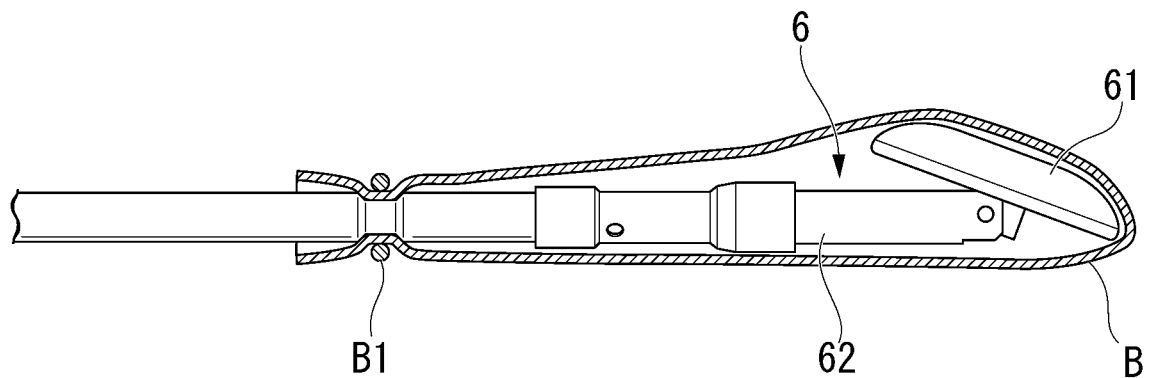
FIG. 14 is a view illustrating a modification example of the anvil kit of the delivery system.

FIG. 14 is a view illustrating a modification example of the anvil kit 6 of the delivery system 100.

For example, in the above embodiment, the anvil kit 6 is directly attached to the tube body 7. However, the aspect of the anvil kit to be used for the method for anastomosing an alimentary tract according to the invention is not limited to this. The anvil kit may be covered with a protective bag B, for example, as illustrated in FIG. 14. It is possible to prevent displeasure to a patient and damage to a mucous membrane of a tissue due to the anvil kit coming into contact with the inside of a lumen when the anvil kit is delivered up to the predetermined anastomosis position. After the anvil kit is delivered to the predetermined anastomosis position, a string B1 for fixing the protective bag B to the tube body 7 is cut by scissors forceps or the like.

Modification Example 3

Figure 15:
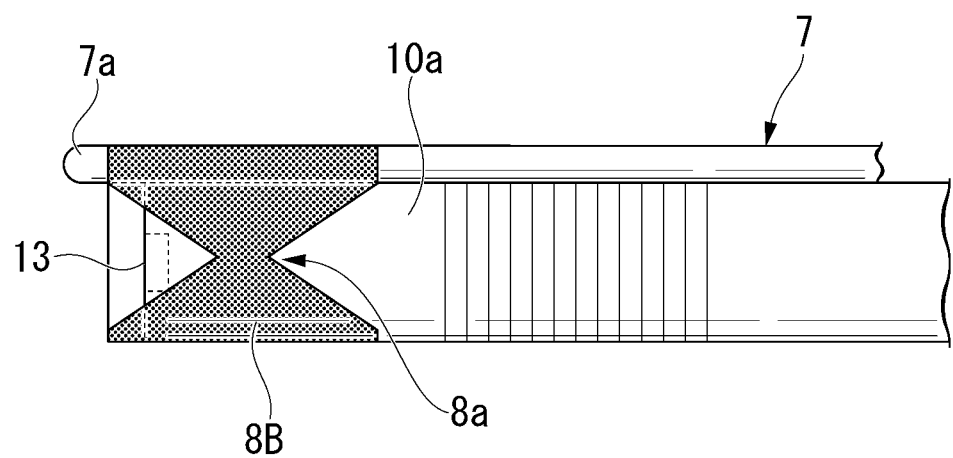
FIG. 15 is a view illustrating a modification example of a binding band of the delivery system.

FIG. 15 is a view illustrating a modification example of the binding band 8 of the delivery system 100.

For example, in the above embodiment, the binding band 8 is formed in a ring shape of a fine diameter. However, the aspect of the binding band to be used for the method for anastomosing an alimentary tract according to the invention is not limited to this. The binding band may be formed to be broad in the longitudinal axis direction of the distal end part 10*a* of the endoscope 1, for example, as in a binding band 8B that is a modification example illustrated in FIG. 15. Similarly to the binding band 8, the binding band 8B is provided with the easily breakable part 8a. Since a distal end of the binding band 8B is located nearer to the distal end side than the imaging unit 13 of the endoscope 1, this distal end is imaged by the imaging unit 13. The surgeon can check whether or not the binding band 8B is broken by checking an image of the binding band 8B captured by the imaging unit 13.

Modification Example 4

Figure 16:
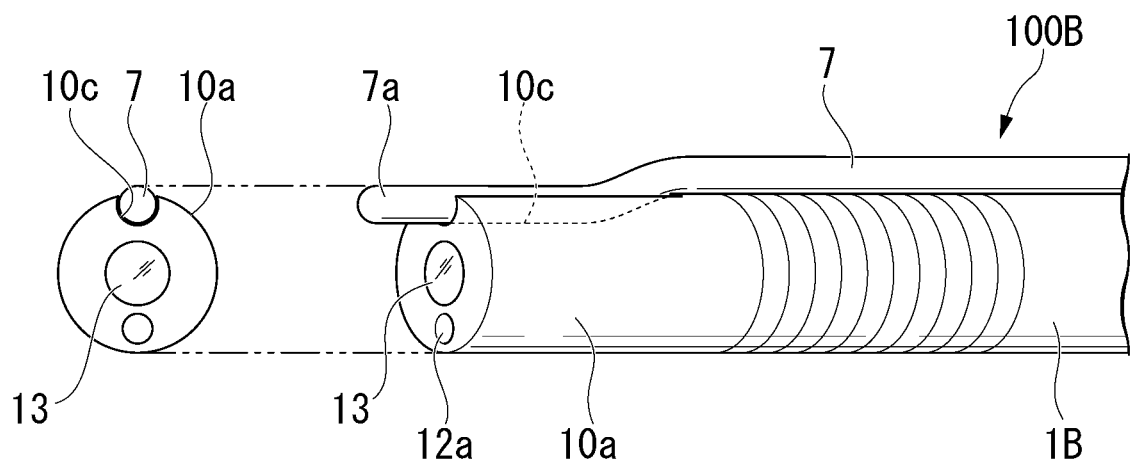
FIG. 16 is a view illustrating a modification example of the delivery system.

FIG. 16 is a view illustrating a modification example of the delivery system 100.

For example, in the above embodiment, the tube body 7 and the endoscope 1 are coupled together by the binding band 8. However, the aspect of the delivery system to be used for the method for anastomosing an alimentary tract according to the invention is not limited to this. The delivery system may not include the binding band like the delivery system 100B that is a modification example of the delivery system 100 illustrated in FIG. 16. In an endoscope 1B of the delivery system 100B, a C channel 10c opening to an outer periphery is formed along the insertion part 10 from the distal end part 10a. The tube body 7 is fitted and coupled to the C channel 10c. The tube body 7 can be detached from the C channel 10c by being pulled by the grasping forceps.

Second Embodiment

A second embodiment of the invention will be described with reference to FIGS. 17 and 18. In the subsequent description, the same components as those already described will be designated by the same reference signs and the redundant description thereof will be omitted. A method for anastomosing an alimentary tract according to the second embodiment is different from that of the first embodiment in terms of the treatment part to be delivered. In the method for anastomosing an alimentary tract according to the present embodiment, the treatment part to be delivered is not the anvil kit 6 but an extension stent 9.

Figure 17:
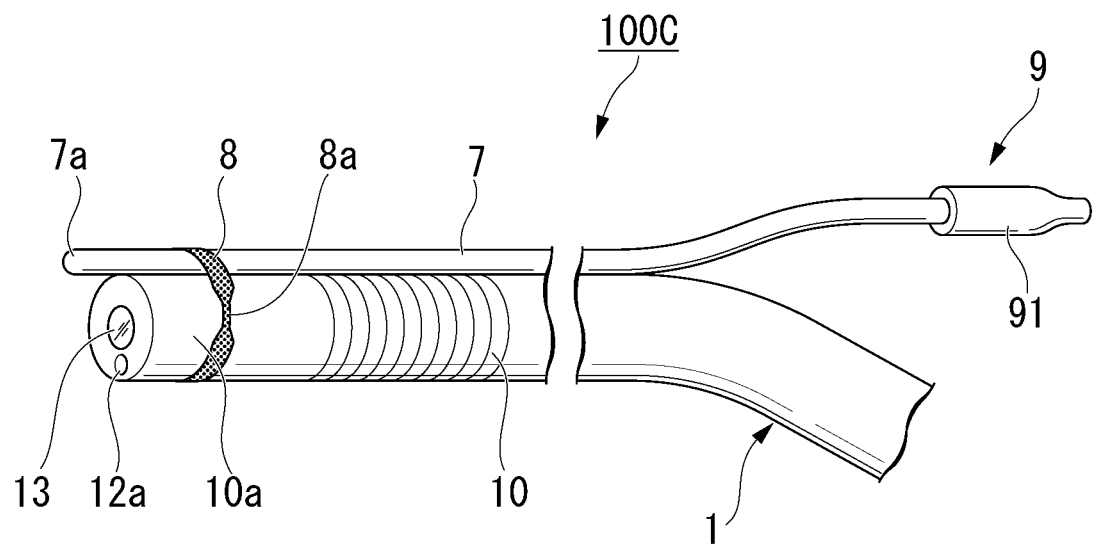
FIG. 17 is a view illustrating a configuration of a delivery system to be used in a method for anastomosing an alimentary tract according to a second embodiment of the invention.

FIG. 17 is a view illustrating the configuration of a delivery system 100C to be used in the method for anastomosing an alimentary tract according to the present embodiment. The delivery system 100C to be used in the method for anastomosing an alimentary tract according to the present embodiment includes the endoscope 1, the tube body 7, and the extension stent 9.

The extension stent (treatment part) 9 is stored in a diameter-reduced state in a case 91 provided at the distal end of the tube body 7. Through the same method as the first step to the sixth step of the first embodiment, the surgeon delivers the case 91, where the extension stent 9 is stored, to a position where the extension stent 9 is detained.

Figure 18:
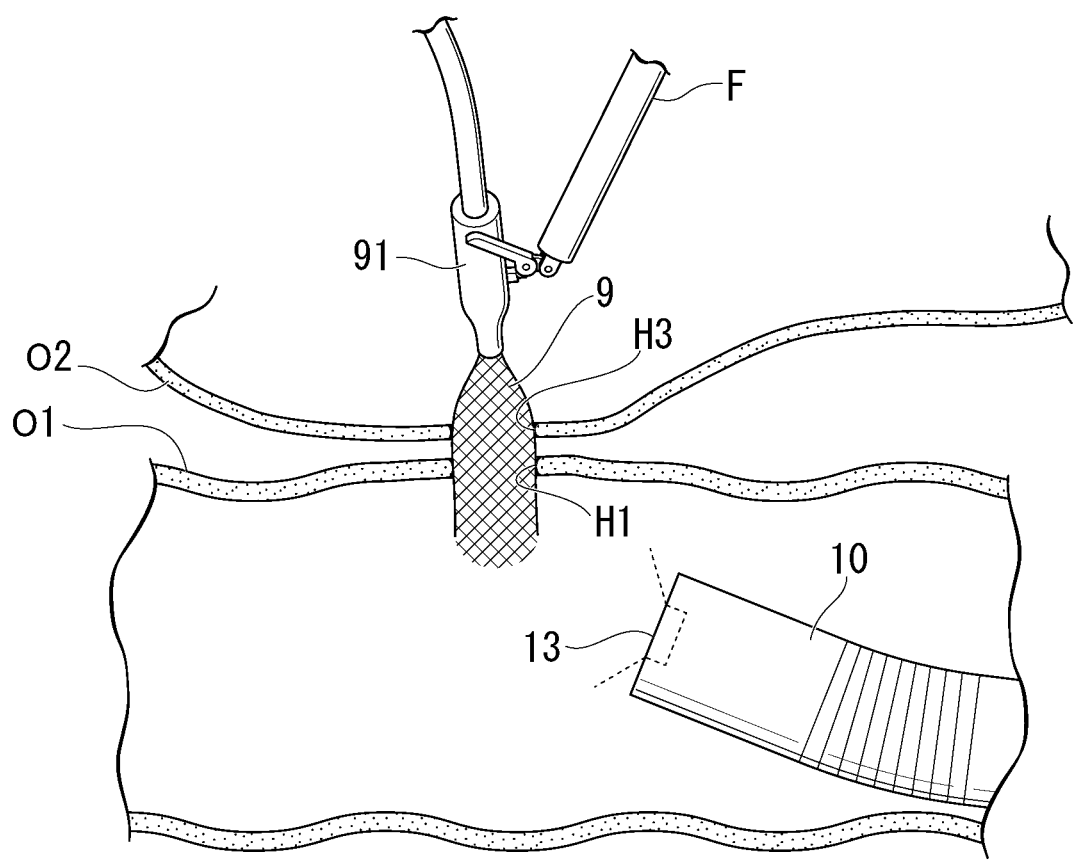
FIG. 18 is a view illustrating the seventh step of anastomosing separate tissues of the method of anastomosing an alimentary tract with an extension stent.

FIG. 18 is a view illustrating the seventh step of anastomosing separated tissues (O1, O2) with the extension stent 9.

The surgeon brings the hole H1 formed in the tissue O1 and the hole H3 formed in the tissue O2 close to each other using a guide wire. The surgeon discharges and detains the extension stent 9 from the case 91 so as to be engaged with both the hole H1 and the hole H3.

According to the method for anastomosing an alimentary tract of the present embodiment, the extension stent (treatment part) 9 can be easily delivered to the predetermined anastomosis position.

Although the second embodiment of the invention has been described above in detail with reference to the drawings, a specific configuration is not limited to the embodiment, and design changes are also included without departing from the scope of the invention. Additionally, the constituent elements illustrated in the above-described embodiment and modification examples can be suitably configured in combination.

The invention claimed is:

1. A method for anastomosing an alimentary tract, using an endoscope, and a tube body having a distal end part and a proximal end part, the distal end part being coupled to an outer periphery of a distal end part of the endoscope, and the proximal end part being provided with a treatment part that is configured to treat a tract wall of an alimentary tract, the method comprising:
  a first step of inserting the endoscope into the alimentary tract through a natural opening in a state where the distal end part of the tube body is coupled to the outer periphery of the distal end part of the endoscope;
  a second step of making a hole in the tract wall of the alimentary tract to allow an abdominal cavity and an inside of the alimentary tract to communicate with each other, the hole being formed in a first portion of the alimentary tract;
  a third step of moving the distal end part of the endoscope to insert the tube body through the hole;
  a fourth step of grasping the distal end part of the tube body disposed through the hole by grasping forceps percutaneously introduced into the abdominal cavity;
  a fifth step of separating the tube body from the outer periphery of the distal end part of the endoscope by moving the distal end part of the endoscope in a direction away from the grasping forceps in a state where the distal end part of the tube body is grasped by the grasping forceps; and
  a sixth step of delivering the treatment part up to the hole by pulling the tube body with the grasping forceps after the fifth step.

2. The method for anastomosing an alimentary tract according to claim 1,
  wherein the second step includes:
    lifting up an outer wall of the alimentary tract by pressing the distal end part of the tube body against an inner wall of the alimentary tract; and
    specifying a position where the outer wall of the alimentary tract is lifted up, and forming the hole at the position where the outer wall is lifted up, with an incision tool percutaneously introduced into the abdominal cavity.

3. The method for anastomosing an alimentary tract according to claim 1,
  wherein the treatment part includes an anvil head capable of receiving staple needles to be discharged from a stapler body, and an anvil shaft extending from the anvil head,
  the method further comprising:
  a step of inserting the anvil shaft through the hole after the sixth step;
  a step of separating the tube body and the treatment part from each other in a state where the anvil shaft is inserted through the hole;
  a step of inserting the stapler body into a separate portion of the alimentary tract; and
  a step of anastomosing the first portion of the alimentary tract and the separate portion of the alimentary tract by discharging the staple needles from the stapler body to the anvil head in a state where the anvil shaft and the stapler body are coupled together within the separate portion of the alimentary tract after the tube body and the anvil shaft are separated from each other.

4. The method for anastomosing an alimentary tract according to claim 1,
wherein the treatment part includes an anvil head capable of receiving staple needles discharged from a stapler body, and an anvil shaft extending from the anvil head, and
wherein the sixth step includes pulling the tube body by the grasping forceps, which grasps the tube body, until the anvil head abuts against an inner surface of the tract wall of the alimentary tract around the hole.

\* \* \* \* \*